United States Patent [19]

Cabri et al.

[11] Patent Number: 5,587,495
[45] Date of Patent: Dec. 24, 1996

[54] 4-SUBSTITUTED ANTHRACYCLINONES AND ANTHRACYCLINE GLYCOSIDES AND THE PROCESS FOR PREPARING THEM

[75] Inventors: Walter Cabri; Silvia De Bernardinis, both of Milan; Franco Francalanci, Novara; Sergio Penco, Milan, all of Italy

[73] Assignee: Farmitalia Carlo Erba Srl, Milan, Italy

[21] Appl. No.: 678,352

[22] PCT Filed: Oct. 24, 1989

[86] PCT No.: PCT/EP89/01266

§ 371 Date: Apr. 25, 1991

§ 102(e) Date: Apr. 25, 1991

[87] PCT Pub. No.: WO90/04601

PCT Pub. Date: May 3, 1990

[30] Foreign Application Priority Data

Oct. 25, 1988 [GB] United Kingdom .............. 8824947

[51] Int. Cl.$^6$ .................................. C07H 15/24
[52] U.S. Cl. .................................. 552/220; 552/208
[58] Field of Search .................................. 552/208, 220; 514/459

[56] References Cited

U.S. PATENT DOCUMENTS 4,154,745  5/1979  Kende et al. .............. 424/180

FOREIGN PATENT DOCUMENTS

| 146542B | 10/1983 | Denmark . |
| 63590 | 3/1983 | Finland . |
| 2601785 | 7/1976 | Germany . |
| 8501726 | 4/1985 | WIPO . |

OTHER PUBLICATIONS

Krohn, K et al Liebigs. Ann. Chem. (10) 943–8 1988.
D. G. Strauss, Die Pharmazie 42 (1987), pp. 289–303, "Strukturen der Anthracyclin–Tumoristatica".
Yasue Matsuzawa, et al; The Journal of Antibiotics, Dec. 1981, pp. 1596–1607 "Structure Activity Relationships and Anthracyclines Relative to Cytotoxicity and Effects to Macromolecular Synthesis in L1210 Lukemia Cells".
Kenneth T. Douglas, Chemistry and Industry, Nov. 5, 1984, pp. 766–769 "Anti Cander Drugs, DNA–Intercalation and Free Radical Attack".
Rolland E. Dolle, et al, J. Chem. Soc. Chem. Commun., 1987, pp. 904 & 905 "Polladium Catalysed Alkyxycarbonylation of Phenols to Benzoate Esters".

*Primary Examiner*—Paul J. Killos
*Attorney, Agent, or Firm*—Oblon, Spivak, McClelland, Maier, & Neustadt, P.C.

[57] ABSTRACT

4-substituted anthracyclinones of formula (I):

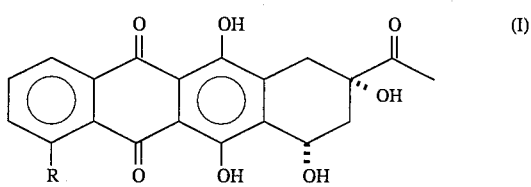

wherein R represents a straight or branched alkyl, alkenyl or alkynyl group of up to 16 carbon atoms optionally substituted by (a) an aryl group which is unsubstituted or substituted by an inert group such as an alkyl, alkoxy or nitro group; (b) an alkoxy group; (c) a trialkylsilyl group, (d) an ester group or (e) an amido group, are intermediates in the preparation of antitumor anthracycline glycosides of formula (IX):

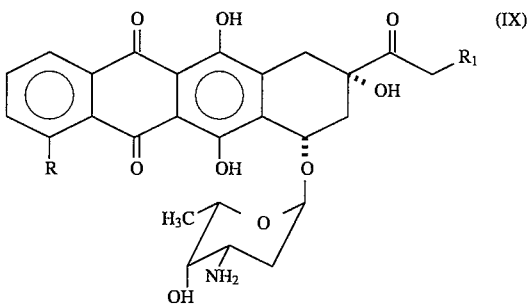

wherein R is as defined above and $R_1$ is a hydrogen atom or a hydroxy group, and pharmaceutically acceptable salts thereof.

16 Claims, No Drawings

4-SUBSTITUTED ANTHRACYCLINONES AND ANTHRACYCLINE GLYCOSIDES AND THE PROCESS FOR PREPARING THEM

This application is a 35 USC 371 of PCT/EP89/0/266 filed Oct. 24, 1989.

The present invention relates to anthracyclinone intermediates and to anthracycline glycosides obtainable therefrom.

According to the present invention, there are provided 4-substituted anthracyclinones of formula (I):

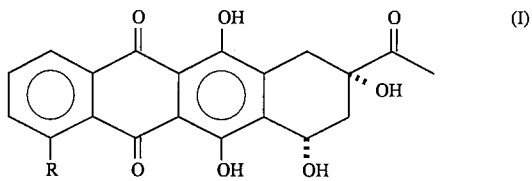

wherein R represents a straight or branched alkyl, alkenyl or alkynyl group of up to 16 carbon atoms, preferably of up to 4 carbon atoms, optionally substituted by (a) an aryl group which is unsubstituted or substituted by an inert group such as alkyl, alkoxy or nitro; (b) an alkoxy group; (c) a trialkylsilyl group; (d) an ester group or (e) an amido group.

The anthracyclinones of formula (I) are intermediates in the preparation of antitumor anthracycline glycosides. Accordingly the present invention further provides anthracycline glycosides having the formula (IX):

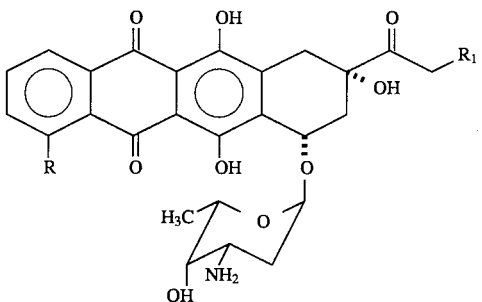

wherein R is as defined above and $R_1$ is a hydrogen atom or a hydroxy group; and their pharmaceutically acceptable salts. Preferred acid addition salts are the hydrochloride salts.

The anthracyclinones of formula (I) and anthracycline glycosides of formula (IX) have a carbon-carbon bond at position C-4. In the definition of radical R, an aryl group is preferably phenyl. Alkyl and alkoxy groups are typically $C_1$–$C_4$ alkyl and $C_1$–$C_4$ alkoxy groups respectively. The ester group (d) is typically a ($C_1$–$C_4$ alkoxy) carbonyl group. The amido group (e) is typically carbamoyl. The alkyl, alkenyl or alkynyl group may be substituted at one or more carbon(s) in the chain by a said group (a) to (e).

Preferred groups which R may represent are vinyl (ethenyl), allyl (propenyl, e.g. 2'-propenyl) trimethylsilylethynyl, trimethylsilylvinyl, phenylethynyl or an alkoxycarbonylvinyl group such as 2'-methoxycarbonylvinyl. The substituents are preferably attached to the 2'-carbon atom of the vinyl or ethynyl group and to the 3'-carbon atom of an allyl group.

Preferred compounds of formula (I) are selected from 4-demethoxy-4-ethenyl-daunomycinone, 4-demethoxy-4'-(2'-methoxycarbonyl)-ethenyl-daunomycinone, 4-demethoxy-4-trimethylsilylethynyl-daunomycinone and 4-demethoxy-4-(2'-propenyl)-daunomycinone. Preferred compounds of formula (IX) are 4-demethoxy-4-ethenyl-daunomycin and its hydrochloride.

The compounds of general formula (I) are obtained from 4-sulfonyl anthracyclinones of formula (II):

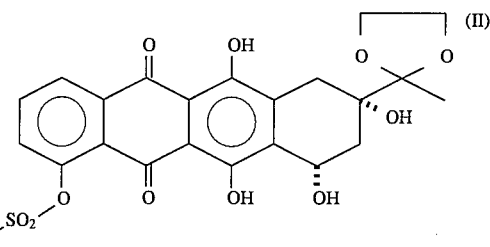

wherein R' represents an alkyl group having from 1 to 10 carbon atoms optionally substituted by one or more halogen atoms or an aryl group optionally substituted by halogen, alkyl, alkoxy or nitro. Preferred groups which R' may represent are trifluoromethyl, 4-fluorophenyl and 4-tolyl. A carbon atom or chain is introduced at position C-4 under mild conditions to give compounds of formula (I) otherwise accessible only by total chemical synthesis. Moreover it is noteworthy that none of the remaining functional groups is affected by the reaction and the stereochemistry at C-7 and C-9 is completely preserved.

Accordingly, the present invention provides a process for the preparation of a 4-substituted anthracyclinone of formula (I), which process comprises reacting a 4-demethyl-4-sulfonyl-13-dioxolanyl daunomycinone of formula (II) with:

(i) an unsaturated compound of formula (IIIa):

wherein R" is an alkenyl or alkynyl group of up to 16 carbon atoms optionally substituted by a said group (a) to (e), or (ii) an organometallic compound of general formula (IIIb)

wherein M represents a metal atom, R is as defined above, n and m may each vary from 0 to 4 but n is not 0, and Y may be a halogen atom or a straight or branched alkyl group having 1 to 6 carbon atoms, in the presence of a catalytic amount of a compound of formula (IV) (hereunder referred to as catalyst):

wherein M' represents a transition metal atom, L and L', which are the same or different, each represent an anion such as Cl⁻ or $CH_3COO^-$ or a neutral molecule as a solvent molecule, a mono- or a di-phosphine, a phosphite or a diamine, and p and q may vary from 0 to 4, to obtain a compound of formula (VI):

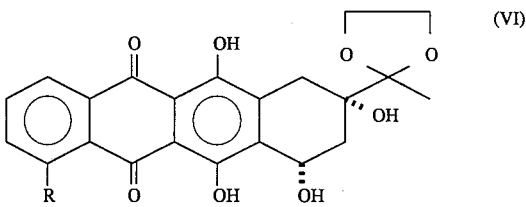

wherein R is as defined above; and removing the 13-oxo protecting group by acid hydrolysis.

In the compound of formula (IV), preferred transition metal atoms which M' may represent are palladium or nickel. Preferred groups which L and/or L' may represent are chelating diphosphines such as 1,3-diphenylphosphinopropane, 1,1'-(diphenylphosphino)ferrocene and 1,2-bis-[N-(1-phenyethyl), N-(diphenylphosphino)amino]ethane. Typically M+n is at least 1, for example 1, 2, 3 or 4. The compound of formula (IV) is therefore a transition metal complex, preferably one between a transition metal atom such as palladium or nickel and a chelating agent such as above. The molar ratio of transition metal atom: chelating ligand is typically from 1:1 to 1:4.

The compound of formula (IIIa) are unsaturated compounds capable of undergoing a Heck-type reaction. Preferred unsaturated molecules which may be used are those known to undergo the Heck-type reaction [R. F. Heck, Org. React. 27 (1982) 345]; in particular trimethylsilyl acetylene, phenylacetylene, alkyl acrylates and vinyl trimethylsilane.

For compounds of formula (IIIb), preferred metal atoms which M may represent are tin, zinc, cadmium and magnesium. Typically n is 1, 2, 3 or 4 whilst m may be 0, 1, 2, 3 or 4. The sum of m and n depends on the valency of M. When Y is a halogen atom, it may be chlorine, bromine or iodine. When Y is an alkyl group it may be methyl.

Compounds of formula (II) can be prepared from naturally occurring daunomycinone (V) as described in EP-A-0288268 and in European Application No. 89303418.1.

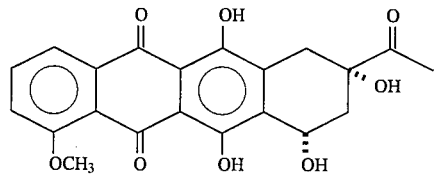

The present invention allows therefore compounds of formula (I) to be synthesised in good yields and with high optical and chemical purity, directly from daunomycinone as summarized in Scheme 1.

The process of the invention may be carried out as follows. Compounds of formula (II) are dissolved in an appropriate polar solvent and added, under an inert atmosphere, to a solution of catalyst, either preformed or generated "in situ" from suitable precursors, in the presence of an unsaturated compound (IIIa) able to undergo the Heck-type reaction or of an organometallic compound of formula (IIIb), and optionally in the presence of a suitable base such as a trialkylamine. The temperature of the reaction is

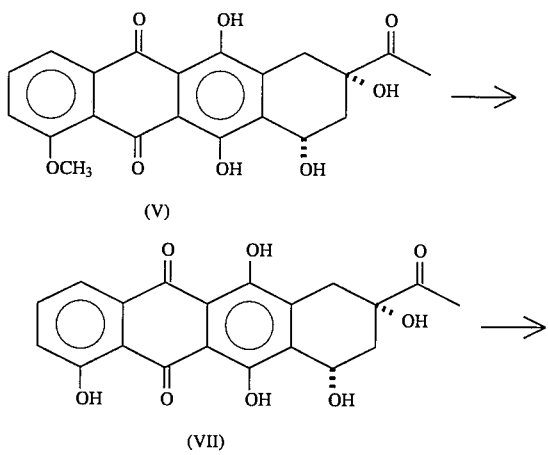

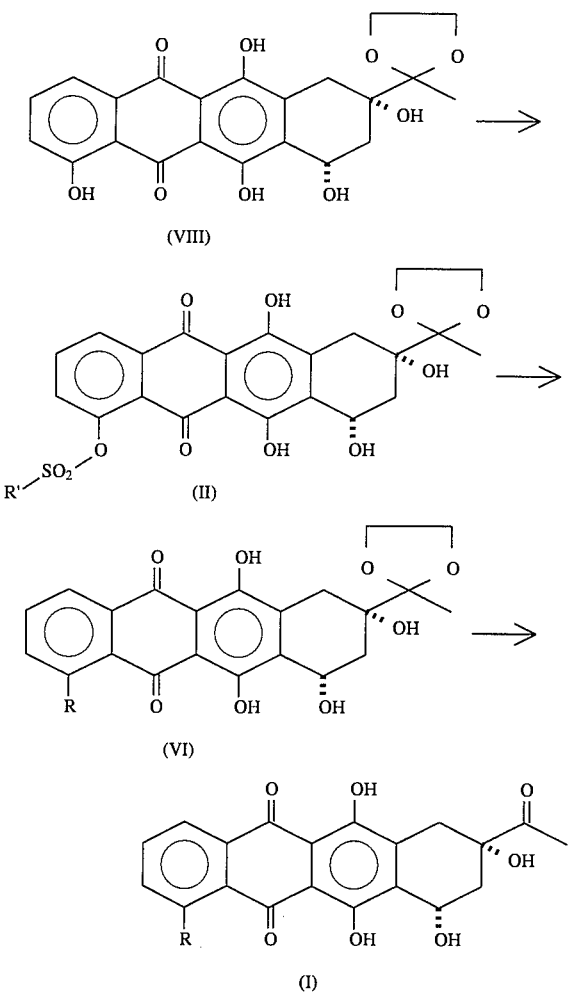

from 0° to 150° C., preferably from 30° to 100° C., and the catalyst is used in a molar ratio to (II) of from 1:1 to 1:10000, preferably from 1:20 to 1:1000.

The compounds of general formula (VI) thus obtained are easily transformed into the final products (I) by acid hydrolysis of the protecting group at the C-13 carbonyl, for example at 0° C. and for 45 minutes with trifluoroacetic acid. The crude compound of formula (I) thus obtained can be purified by chromatography on a silica gel column using as the eluent system chloroform:acetone (95:5 v/v).

The palladium-catalyzed arylation of unsaturated compounds (the Heck reaction) by using aryl halides has been known for a long time and many papers and patents dealing with its use in organic chemistry have been published [a) R. F. Heck, Org. React. 27 (1982) 345; b) A. Spencer, J. Organomet. Chem. 258 (1983) 101; c) T. Jeffery, J. Chem. Soc. Chem. Commun. (1984) 1287; d) L. Crombie, M. A. Horsham, Tetrahedron Lett. 28 (1987) 4879]; much less work is reported in the scientific literature as far as aryl sulfonates are used as arylating compounds [Q. Y. Chen, Z. Y. Yang, Tetrahedron Lett. 27 (1986) 1171; J. W. Tilley, S. Zawoiski, J. Org. Chem. 53 (1988) 386]. Also the palladium or nickel-catalyzed coupling of aryl halides or sulfonates with organometallic compounds has been known for several years [M. Kumada, Pure Appl. Chem. 52 (1980) 669; Q. Y. Chen, Y. B. He, Tetrahedron Lett. 28 (1987) 2387; A. M. Echevarren, J. K. Stille, J. Am. Chem. Soc. 109 (1987) 5478].

However both classes of reactions have never been reported in the anthracycline chemistry, probably because of the presence of other interfering functional groups. The problems arising from the presence of said groups, namely aromatization of ring A, formation of 7-deoxy derivatives, hydrolysis of 4-sulfonyl derivatives and/or modifications of the quinone moiety can be suppressed under the conditions of the invention.

The present invention also provides a process for the preparation of an anthracycline glycoside of formula (IX) or a pharmaceutically acceptable salt thereof, which process comprises:

(i) reacting a 4-substituted anthracyclinone of formula (I) with a halosugar of formula (X):

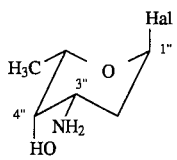

(X)

wherein Hal represents a halogen atom, the 3"-amino group is protected or unprotected and the 4"-hydroxy group is protected or unprotected, and, if present, removing the or each protecting group from the product thus-obtained such as to obtain an anthracycline glycoside of formula (IX) wherein $R_1$ is a hydrogen atom;

(ii) if desired, converting the said glycoside of formula (IX) thus obtained into a pharmaceutically acceptable salt thereof;

(iii) if desired, brominating the said glycoside of formula (IX) or pharmaceutically acceptable salts thereof and hydrolysing the 14-bromo derivative thus obtained so as to form the corresponding glycoside of formula (IX) wherein $R_1$ is a hydroxy group and;

(iv) if desired, converting the said glycoside of formula (IX) wherein $R_1$ is hydroxy into a pharmaceutically acceptable salt thereof.

Preferably the anthracyclinone of formula (I) is reacted with the halosugar of formula (X) in step (i) in an inert organic solvent under an inert atmosphere at a temperature of from 5° to 30° C. and in the presence of silver trifluoromethanesulfonate; if desired, the resulting anthracycline glycoside is isolated in step (ii) as its hydrochloride by treatment with methanolic hydrogen chloride; if desired, step (iii) is effected by bromination and by hydrolysis of the 14-bromo derivative thus obtained and, if desired, the resulting anthracycline glycoside is isolated in step (iv) as its hydrochloride by treatment with methanolic hydrogen chloride.

An anthracycline glycoside of formula (IX) in which $R_1$ is a hydrogen atom is therefore prepared by reacting an anthracyclinone of formula (I) with a halosugar of formula (X). In formula (X), Hal is typically a chlorine atom. If the 3"-amino group is protected, the protecting group may be a trifluoroacetyl group. If the 4"-hydroxy group is protected, the protecting group may also be a trifluoroacetyl group. The condensation of the anthracyclinone of formula (I) and halosugar of formula (X) generally takes place in the presence of silver trifluoromethanesulfonate (triflate).

The anthracyclinone may be dissolved in an inert organic solvent such as methylene dichloride, with the reaction taking place under an inert atmosphere such as argon at a temperature of from 5° to 30° C., typically at ambient temperature. Any protecting groups may be removed by mild alkaline hydrolysis, for example by treatment with 0.1N aqueous sodium hydroxide. Preferably the anthracycline glycoside is isolated as its hydrochloride by treatment of the free base with methanolic hydrogen chloride.

The anthracycline glycoside of formula (IX) in which $R_1$ is a hydrogen atom, or one of its salts, can be converted into the corresponding doxorubicin derivative in which $R_1$ is a hydroxy group by bromination at the 14-position and by hydrolysis of the 14-bromo derivative with aqueous sodium formate. The bromination and hydrolysis conditions are typically those described in U.S. Pat. No. 4,122,076 or GB-A-1217133.

More specifically, the glycoside of formula (IX) in which $R_1$ is a hydrogen atom, or one of its salts, can be reacted with bromine in chloroform to obtain a 14-bromo derivative from which, after hydrolysis at room temperature and for 48 hours under nitrogen with an aqueous solution of sodium formate, the compound of formula (IX) in which $R_1$ is hydroxy is obtained as a free base and, by treatment with anhydrous methanolic HCl, is isolated as its hydrochloride.

The invention provides pharmaceutical composition comprising an anthracycline glycoside of formula (IX) or a pharmaceutically acceptable salt thereof, together with a pharmaceutically acceptable diluent or carrier. Conventional carriers and diluents may be used. The composition may be formulated and administered in conventional manner.

The compounds of the invention are useful as antitumor agents in vitro. An amount sufficient to inhibit the growth of the tumour may be administered. The tumor may be a Colon adenocarcinoma or Gross leukaemia tumor.

The following Examples illustrate the invention.

EXAMPLE 1

4-Demethoxy-4-ethenyl daunomycinone [(I), R=CH=CH$_2$

To a solution of 1 g of 4-demethyl-4-trifluoromethansulfonyl-13-dioxolanyl daunomycinone [(II), R'=CF$_3$] (1.78 mmol) in 50 ml of dioxane, under an inert atmosphere, were successively added 1.55 ml of diisopropylethylamine, 0.3 ml of acetic acid, 55 mg of 1,1'bis-(diphenylphosphino)-ferrocene (0.097 mmol), 20 mg of palladium acetate (0.089 mmol) and 3.52 g of vinyltrimethyl silane (35.2 mmol). The reaction mixture was stirred at 60° C. overnight, then cooled to 0° C., acidified with 10% hydrochloric acid and extracted with methylene chloride. The organic phase was evaporated to dryness leaving the crude 4-demethoxy-4-(2'-trimethylsilyl)ethenyl-13-dioxolanyl daunomycinone [(VI), R=CH=CH—Si(CH$_3$)$_3$].

$^1$H-NMR 300 MHz (in CDCl$_3$): δ=0.24 (9H, s), 1.47 (3H, s), 1.95 (1H, dd, J=5.0;14.6 Hz), 2.44 (1H, d, J=14.6 Hz), 2.73 (1H, d, J=18.9), 3.18 (1H, dd, J=2.5;18.9), 3.29 (1H, s), 3.8 (1H, d, J=6.6 Hz), 4.08 (4H, s), 5.2 (1H, t, J=5.0 Hz), 6.32 (1H, d, J=18.9 Hz), 7.69 (1H, t, J=7.7 Hz)), 7.80 (1H, dd, J=1.0;7.7 Hz), 7.96 (1H, d, J=18.9 Hz), 8.24 (1H, dd, J=1.3;7.7 Hz), 13.24 (1H, s), 13.75 (1H, s).

U.V. (in EtOH): λ=526, 492, 359, 256, 214 nm; λmax= 256 nm

I.R. (KBr pellet): ν=3480, 1512, 1585, 1575 cm$^{-1}$

[α]$_D^{20}$(c=0.1 in dioxane)=+179° M.S. m/z=510 (M$^+$,base peak) TLC on Kieselgel plate F 254 (Merck) using chloroform/acetone (9:1 by volume) Rf=0.72

The crude [(VI), R=CH=CH—Si(CH$_3$)$_3$] was stirred at 0° C. in 6 mL of trifluoroacetic acid and 0.4 mL of water for 45 minutes. The reaction mixture was diluted with 150 mL of water and extracted with methylene chloride. The organic layer was washed with saturated sodium bicarbonate and water till neutrality, dried over sodium sulfate and evaporated to dryness. The residue was chromatographated on silica gel (chloroform/acetone 95:5 by volume as eluant) obtaining 0.45 g [64% from (II), R'=CF$_3$], of 4-demethoxy-4-ethenyl daunomycinone [(I), R=CH=CH$_2$], (HPLC 97.8%).

HPLC analysis: Column: Merck RP 18/7 μm (250×4.2 mm), Mobile phase:

| A | 0.01M sodium heptansulfonate/0.02M phosphoric acid | 6 |
|---|---|---|
|   | Acetonitrile | 4 |
| B | Methanol | 7 |
|   | Acetonitrile | 3 |

Gradient: from 20% B to 70% B in 25 min, Flow rate: 1.5 mL/min, Detector: UV at 254 nm.

$^1$H-NMR 300 MHz (in CDCl$_3$): δ=2.15 (1H, dd, J=4.8;14.5 Hz), 2.35 (1H, dt, J=2.0;14.5 Hz), 2.42 (3H, s), 2.95 (1H, d, J=18.6 Hz), 3.20 (1H, dd, J=2.0;18.6 Hz), 3.75 (1H, d, J=5.7 Hz), 4.53 (1H, s), 5.32 (1H, m), 5.51 (1H, dd, J=1.4;11.0 Hz), 5.64 (1H, dd, J=1.4;17.3 Hz), 7.74–7.92 (3H, m), 8.37 (1H, dd, J=2.0;7.5 Hz), 13.28 (1H, s), 13.71 (1H,s).

U.V. (in EtOH): λ=525, 491, 356, 256, 212 nm; λmax=256 nm.

I.R. (KBr pellet): ν=3480, 1712, 1610, 1575 cm$^{-1}$.

$[α]_D^{20}$(c=0.1 in dioxane)=+190° M.S. m/z=394 (M$^+$,base peak) TLC on Kieselgel plate F 254 (Merck) using chloroform/acetone (9:1 by volume) Rf=0.67

EXAMPLE 2

4-Demethoxy-4-ethenyl daunomycinone [(I), R=CH=CH$_2$]

The reaction was carried out as described in example 1, except that diphenylphosphinopropane (40 mg, 0.097 mmol) was used as ligand for palladium obtaining the crude 4-demethoxy-4-(2'trimethylsilyl)ethenyl-13-dioxolanyl daunomycinone [(VI), R=CH=CH—Si(CH$_3$)$_3$].

The crude [(VI), R=CH=CH—Si(CH$_3$)$_3$] was treated with trifluoroacetic acid as described in example 1 obtaining, after chromatography on silica gel (chloroform/acetone 95:5 by volume as eluant) 0.41 g [58.3% from (II), R'=CF$_3$] of 4-demethoxy-4-ethenyl daunomycinone [(I), R=CH=CH$_2$] (HPLC 98.2%).

EXAMPLE 3

4-Demethoxy-4-(2'-methoxycarbonyl) ethenyl daunomycinone [(I), R=CH=CH—COOCH$_3$]

The reaction was carried out as described in example 1 except that methyl acrylate (3.17 mL, 35.2 mmol) was used as reactant, obtaining the crude 4-demethoxy-4-(2'-methoxycarbonyl)ethenyl-13-dioxolanyl daunomycinone [(VI), R=CH=CH—COOCH$_3$].

$^1$H-NMR 300 MHz (in CDCl$_3$): δ=1.48 (3H, s), 1.98 (1H, dd, J=5.1;14.7 Hz), 2.46 (1H, dt, J=2.0;14.7 Hz), 2.79 (1H, d, J=18.9 Hz), 3.24 (1H, dd, J=2.1;18.9 Hz), 3.34 (1H, s), 3.87 (4H, s), 4.08 (4H, s), 5.26 (1H, dd, J=1.5;4.9 Hz), 6.24 (1H, d, J=15.9 Hz), 7.75–7.80 (2H, m), 8.36–8.44 (1H, m), 8.72 (1H, d, J=15.9 Hz), 13.35 (1H, s), 13.54 (1H, s).

U.V. (in EtOH): λ=527, 492, 347, 264, 213 nm; λmax=264 nm

I.R. (KBr pellet): ν=3470, 1716, 1610, 1575 cm$^{-1}$.

$[α]_D^{20}$(c=0.1 in dioxane)=+195° M.S. m/z=496 (M$^+$, base peak) TLC on Kieselgel plate F 254 (Merck) using chloroform/acetone (9:1 by volume) Rf=0.44

The crude [(VI), R=CH=CH—COOCH$_3$] was treated with trifluoroacetic acid as described in example 1 obtaining, after chromatography on silica gel (chloroform/acetone 95:5 by volume as eluant) 0.41 g [50.8% from (II), R'=CF$_3$], of 4-demethoxy-4-(2'-methoxycarbonyl)ethenyl daunomycinone, [(I) R=CH=CH—COOCH$_3$], (HPLC 97.8%).

$^1$H-NMR 300 MHz (in CDCl$_3$): δ=2.16 (1H, dd, J=5.0;14.8 Hz), 2.36 (1H, dt, J=2.2;14.8 Hz), 2.43 (3H, s), 2.95 (1H, d, J=18.8 Hz), 3.21 (1H, dd, J=2.2;18.8 Hz), 3.75 (1H, d, J=1.2 Hz), 3.87 (3H, s), 4.55 (1H, s), 5.34 (1H, bs), 6.26 (1H, d, J=15.8 Hz), 7.80–7.90 (2H, m) 8.46 (1H, dd, J=2.9;6.2 Hz), 8.75 (1H, d, J=15.8 Hz), 13.24 (1H, s), 13.53 (1H, s).

U.V. (in EtOH): λ=493, 348, 265, 214 nm; λ max=265 nm.

I.R. (KBr pellet): ν=3390, 1713, 1690, 1615, 1575 cm$^{-1}$.

$[α]_D^{20}$ (c=0.1 in dioxane)=+183° M.S. m/z=452 (M$^+$, base peak) TLC on Kieselgel plate F 254 (Merck) using chloroform/acetone (9:1 by volume) Rf=0.61

EXAMPLE 4

4-Demethoxy-4-(2'-methoxycarbonyl)ethenyl daunomycinone [(I), R=CH=CH—COOCH$_3$]

The reaction was carried out as described in example 3, except that dimethylformamide (50 ml) was used as solvent and 1,2-bis-[N-(1 phenylethyl), N-(diphenylphosphino)amino] ethane (62 mg, 0.097 mmol) as ligand for palladium, obtaining, after chromatography on silica gel (chloroform/acetone 95:5 as eluant), 0.34 g [42% from (II), R'=CF$_3$] of 4-demethoxy-4-(2'-methoxycarbonyl)ethenyl daunomycinone [(I), R=CH=CH—COOCH$_3$], (HPLC 98.2%).

EXAMPLE 5

4-Demethoxy-4-trimethylsilylethynyl daunomycinone [(I), R=C=C—Si(CH$_3$)$_3$]

The reaction was carried out as described in example 1, except that trimethylsilyl acetylene (5.9 ml, 35.2 mmol) was used as reactant, obtaining the crude 4-demethoxy-4-trimethylsilylethynyl-13-dioxolanyl daunomycinone [(VI), R=C=C—Si(CH$_3$)$_3$].

$^1$H-NMR 300 MHz (in CDCl$_3$): δ=0.35 (9H, s), 1.48 (3H, s), 1.99 (1H, dd, J=5.0;14.6 Hz), 2.47 (1H, d, J=14.6 Hz), 2.78 (1H, d, J=19.0), 3.15 (1H, bs), 3.23 (1H, dd, J=2.0;19.0 Hz), 3.82 (1H, bs), 4.08 (4H, s), 5.28 (1H, d, J=3.7 Hz), 7.72 (1H, t, J=7.7 Hz), 7.94 (1H, dd, J=1.4;7.7 Hz), 8.34 (1H, dd, J=1.4;7.7 Hz), 13.22 (1H, s), 13.80 (1H, s).

U.V. (in EtOH): λ=528,494,363,269,247,214 nm; λ max=269 nm.

I.R. (KBr pellet): ν=3540, 3470, 1615, 1565 cm$^{-1}$.

$[α]_D^{20}$ (c=0.1 in dioxane)=+183° M.S. m/z=508 (M$^+$, base peak) TLC on Kieselgel plate F 254 (Merck) using chloroform/acetone (9:1 by volume) Rf=0.65

The crude [(VI), R=C=C—Si(CH$_3$)$_3$] was treated with trifluoroacetic acid as described in example 1 obtaining, after chromatography on silica gel (chloroform/acetone 95:5 by volume as eluant) 0.12 g [15% from (II), R'=CF$_3$] of 4-demethoxy-4-trimethylsilylethynyl daunomycinone [(I), R=C=C—Si(CH$_3$)$_3$], (HPLC 96.4%).

$^1$H-NMR 300 MHz (in CDCl$_3$): δ=0.30 (9H, s), 2.04 (1H, dd, J=4.8;14.6 Hz), 2.25 (1H, d, J=14.6 Hz), 2.34 (3H, s), 2.69 (1H, d, J=18.7 Hz), 2.91 (1H, dd, J=1.4;18.7 Hz), 4.06 (1H, d, J=5.6), 4.71 (1H, s), 5.11 (1H, t, J=4.2 Hz), 7.60 (1H, t, J=7.8 Hz), 7.80 (1H, dd, J=1.3;7.7 Hz), 8.03 (1H, dd, J=1.3;7.7 Hz), 12.82 (1H, s), 13.29 (1H, s).

U.V. (in EtOH): λ=493, 366, 269, 246, 222, 204 nm; λ max=269 nm.

I.R. (KBr pellet): ν=3490, 1715, 1615, 1565 cm$^{-1}$ M.S. m/z=464 (M$^+$, base peak) TLC on Kieselgel plate F 254 (Merck) using chloroform/acetone (9:1 by volume) Rf=0.44

EXAMPLE 6

4-Demethoxy-4-(2' propenyl)daunomycinone [(I), R=CH$_2$—CH=CH$_2$]

To a solution of 1 g of 4-demethyl-4-trifluoromethansulfonyl-13-dioxolanyl daunomycinone [(II), R'+CF$_3$] (1.78 mmol) in 50 ml of dioxane, under an inert atmosphere, were successively added 55 mg (0.097 mmol) of 1,1'bis-(diphenylphosphino)ferrocene, 20 mg (0.089 mmol) of palladium acetate and 1.1 mL (3.56 mmol) of allyl trimethyltin. The reaction mixture was stirred at 70° C. overnight, then cooled to 0° C. and worked up as described in example 1 obtaining crude 4-demethoxy-4-(2'propenyl)-13-dioxolanyl daunomycinone [(VI),R=CH$_2$—CH=CH$_2$]

$^1$H-NMR 300 MHz (in CDCl$_3$): δ=1.47 (3H, s), 1.98 (1H, dd, J=5.0;14.7 Hz), 2.45 (1H, dt, J=2.0;14.7 Hz), 2.74 (1H, d, J=18.9 Hz), 3.14 (1H, s), 3.24 (1H, dd, J=2.2;18.9 Hz), 3.78 (1H, d, J=6.8 Hz), 4.06–4.12 (6H, m), 5.00–5.21 (2H, m), 5.23–5.30 (1H, m), 6.00–6.18 (1H, m), 7.60–7.75 (2H, m), 8.31 (1H, dd, J=1.9;7.4 Hz), 13.36 (1H, s), 13.85 (1H, s).

U.V. (in EtOH): λ=523, 489, 339, 287, 254, 207 nm; λmax=254 nm

I.R. (KBr pellet): ν=3470, 3335, 1615, 1575 cm$^{-1}$

[α]$_D^{20}$(c=0.1 in dioxane)=+115° M.S. m/z=452 (M$^+$, base peak) TLC on Kieselgel plate F 254 (Merck) using chloroform/acetone (9:1 by volume) Rf=0.68

The crude [(VI), R=CH$_2$—CH=CH$_2$] was treated with trifluoroacetic acid as described in example 1 obtaining, after chromatography on silica gel (chloroform/acetone 95:5 by volume as eluant) 0.51 g [70% from (II), R'=CF$_3$] of 4-demethoxy-4-(2'propenyl) daunomycinone [(I), R=CH$_2$—CH=CH$_2$], (HPLC 97.9%).

$^1$H-NMR 300 MHz (in CDCl$_3$): δ=2.17 (1H, dd, J=4.8;14.5 Hz), 2.35 (1H, dt, J=2.0;14.5 Hz), 2.43 (3H,s), 2.94 (1H, d, J=18.7 Hz), 3.19 (1H, dd, J=2.2;18.7 Hz), 3.77 (1H, bs), 4.08–4.12 (2H, m), 4.55 (1H, bs), 5.02–5.13 (2H, m), 5.30–5.35 (1H, m), 6.04–6.19 (1H, m), 7.65 (1H, dd, J=1.8;7.7 Hz), 7.74 (1H, t, J=7.7 Hz), 8.33 (1H, dd, J=1.8;7.4 Hz), 13.28 (1H, s) 13.82 (1H, s)

U.V. (in EtOH): λ=489, 339, 286, 254, 208 nm; λmax= 254 nm

I.R. (KBr pellet): ν=3410, 1710, 1618, 1575 cm$^{-1}$

[α]$_D^{20}$ (c=0.1 in dioxane)=+152° M.S. m/z=408 (M$^+$, base peak) TLC on Kieselgel plate F 254 (Merck) using chloroform/acetone (9:1 by volume) Rf=0.78

EXAMPLE 7

Preparation of 4-ethenyl-(4-demethoxy)-daunomycin hydrochloride

To a stirred solution of 4-ethenyl-(4-demethoxy) daunomycinone (0.468 g, 1.2 mmol) in CH$_2$Cl$_2$ (80 ml), at room temperature under argon, a solution of chlorodaunosammine (0.536 g, 1.5 mmol) in CH$_2$Cl$_2$ (10 ml) and a solution of AgCF$_3$SO$_3$ (0.398 g), 1.5 mmol in Et$_2$O (12 ml) were simultaneously added, over a ten minutes period. After 30 minutes, 0.144 ml of pyridine were added and the reaction mixture was filtered on dicalite. The solution was sequentially washed with HCl 1%, water, dried (Na$_2$SO$_4$) and evaporated in vacuo.

The residue was taken with acetone (20 ml), cooled to 0° C. and treated with NaOH 0.075M (100 ml). After an hour CH$_2$Cl$_2$ and water were added and the pH was adjusted to 4 with HCl 3%. The aqueous phase was separated, treated with NH$_4$OH 1% to pH 8, and extracted with CH$_2$Cl$_2$ (3×100). The collected organic phases were dried over Na$_2$SO$_4$ and evaporated in vacuo. The product was purified by SiO$_2$ column chromatography (CH$_2$Cl$_2$/MeOH/CH$_3$COOH/H$_2$O= 180/25/2/3). The collected fractions were diluted with water and the pH adjusted to 8 with NH$_4$OH 1%. The organic phase was separated, dried and evaporated in vacuo to give 0.175 g of free base.

To a solution of the free base, in the minimum amount of CHCl$_3$, 0.11 ml of HCl/MeOH 3N were added. The precipitate was filtered, washed with ether and dried obtaining 0.170 g of the title compound. (HPLC=96.17%) $^3$H-NMR 200 MHz (DMSO-d6): δ(ppm)=1.16 (3H, d; J=6.6 Hz), 1.81 (2H, m), 2.12 (2H, m), 2.27 (3H, s), 2.95 (2H, bs), 3.39 (1H, m), 3.58 (1H, bs), 4.21 (1H, q; J=6.6 Hz), 4.92 (1H, bs), 5.30 (1H, bs), 5.52 (3H, m), 5.73 (1H, d; J=17.26 Hz), 7.85 (3H, m), 8.28 (1H, dd; J=7.05 Hz, J=1.87 Hz), 13.40 (2H bs).

UV (EtOH): =523.6, 489.6, 354.8, 258.4, 213.2 nm. max= 258.4 nm. TLC on Kieselgel plate F 254 (MERCK) using CH$_2$Cl$_2$/MeOH/CH$_3$COOH/H$_2$O (8:2:0.7:0.3 by volume) Rf=0.83

EXAMPLE 8

Preparation of 4-ethenyl-4-(demethoxy) doxorubicin hydrochloride

The title compound can be prepared from 4-ethenyl-4-(demethoxy)-daunomycin hydrochloride according to the procedure described in U.S. Pat. No. 4122076. 0.2 g of the 4-ethenyl-4-(demethoxy)-daunomycin hydrochloride is dissolved in a mixture of anhydrous methanol and dioxane. A solution of 1 g of bromine in 10 ml methylene chloride is added, as described in U.S. Pat. No. 4122076, to afford the 14-bromo derivative. The 14-bromo derivative is hydrolysed at room temperature and for 48 hours under nitrogen with an aqueous solution of sodium formate. 4-Ethenyl-4-(demethoxy)doxorubicin is thus obtained which, by treatment with anhydrous methanolic hydrogen chloride, is isolated as its hydrochloride.

We claim:
1. A 4-substituted anthracyclinone of formula (I):

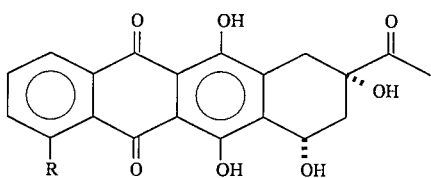

wherein R represents a straight or branched alkenyl of 2 to 4 carbon atoms.

2. The compound according to claim 1, wherein R represents vinyl or allyl.

3. The compound according to claim 1, which is selected from 4-demethoxy-4-ethenyl-daunomycinone, and 4-demethoxy-4-(2'-propenyl)-daunomycinone.

4. A process for the preparation of a 4-substituted anthracyclinone of formula (I):

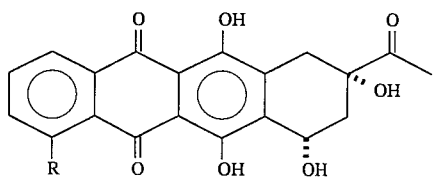

wherein R represents a straight or branched alkenyl group of 2 to 4 carbon atoms, comprising the steps of:

reacting at a temperature of 0° C. to 150° C. a 4-demethyl-4-sulfonyl-13-dioxolanyl daunomycinone of formula (II):

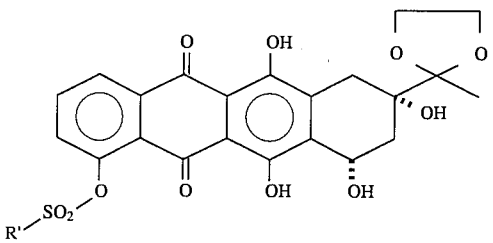

wherein R' represents an alkyl group of from 1 to 10 carbon atoms optionally substituted by one or more halogen atoms or an aryl group optionally substituted by halogen, alkyl, alkoxy or nitro, with (i) an unsaturated compound of formula (IIIa):

 (IIIa)

wherein R" is an alkenyl group of 2 to 4 carbon atoms, or (ii) an organometallic compound of general formula (IIIb)

 (IIIb)

wherein M represents tin, zinc or cadmium, R is as defined above, n and m are independently from 0 to 4, but n is not 0, and Y may be a halogen atom or a straight or branched alkyl group having from 1 to 6 carbon atoms, in the presence of a catalytic amount, which is a molar ratio of 1:1 to 1:10000 to the starting material of formula (II), of a compound of formula (IV):

 (IV)

wherein M' represents palladium or nickel atom, L and L', which are the same or different, each represent Cl⁻, CH₃COO⁻, a solvent molecule, a mono- or di-phosphine, a phosphite or a diamine and p and q are independently 0 to 4, to obtain a compound of formula (VI):

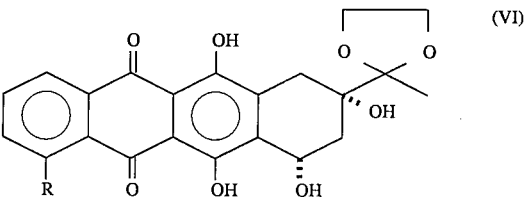

wherein R is as defined above; and, removing the 13-oxo protecting group by acid hydrolysis.

5. The process according to claim 4, wherein the step of removing the 13-oxo protecting group is conducted at 0° C. for 45 minutes using trifluoroacetic acid; and the obtained crude compound of formula (I) is purified by chromatography on a silica gel column using an eluent system of chloroform: acetone (95:5 v/v).

6. A process for the preparation of an anthracycline glycoside of formula (IX):

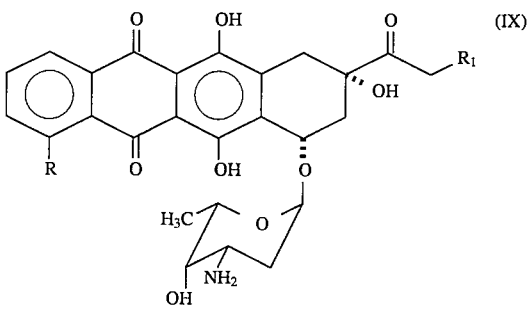

wherein R represents a straight or branched alkenyl group of up to 16 carbon atoms and $R_1$ is a hydrogen atom or a hydroxy group; or a pharmaceutically acceptable salt thereof, comprising the step of:

(i) reacting, in an inert organic solvent under an inert atmosphere at a temperature of from 5° to 30° C. and in the presence of silver trifluoromethanesulfonate, a 4-substituted anthracyclinone of formula (I):

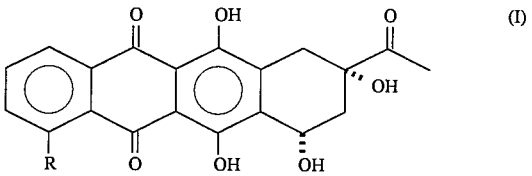

wherein R is as defined above, with a halosugar formula (X):

wherein Hal represents a halogen atom, the 3"-amino group is protected or unprotected and the 4"-hydroxy group is protected or unprotected, and, if present, removing the, or each, protecting group from the resulting product to obtain the anthracycline glycoside of formula (IX) wherein $R_1$ is a hydrogen atom.

7. The process according to claim 6, wherein the inert organic solvent is methylene dichloride.

8. The process according to claim 6, wherein the inert atmosphere is argon.

9. The process according to claim 6, wherein the 3"-amino protecting group is a trifluoroacetyl group.

10. The process according to claim 6, wherein the 4"-hydroxy protecting group is a trifluoroacetyl group.

11. The process according to claim 6, which further comprises:

(ii) converting the glycoside of formula (IX) into a pharmaceutically acceptable salt thereof.

12. The process according to claim 6, further comprising the steps of:

(iii) brominating said glycoside of formula (IX) or pharmaceutically acceptable salt thereof; and, (iv) hydrolysing the 14-bromo derivative obtained in (iii) so as to form the corresponding glycoside of formula (IX) wherein $R_1$ is a hydroxy group.

13. The process according to claim 12, which further comprises:

(v) converting said glycoside of formula (IX) wherein $R_1$ is hydroxy into a pharmaceutically acceptable salt thereof.

14. The process according to claim 11, wherein the anthracycline glycoside formed in step (i) is isolated in step (ii) as its hydrochloride by treatment with methanolic hydrogen chloride.

15. The process according to claim 13, wherein the resulting anthracycline glycoside is isolated in step (v) as its hydrochloride by treatment with methanolic hydrogen chloride.

16. An anthracycline glycoside of formula (IX):

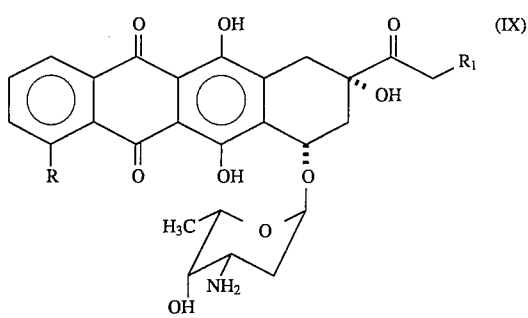

wherein R is as defined in claim 1 and $R_1$ is a hydrogen atom or a hydroxy group; and pharmaceutically acceptable salts thereof.

* * * * *